United States Patent
Cho et al.

(10) Patent No.: US 7,119,332 B2
(45) Date of Patent: Oct. 10, 2006

(54) METHOD OF FABRICATING PROBE FOR SCANNING PROBE MICROSCOPE

(75) Inventors: Il-Joo Cho, Seoul (KR); Eun-Chul Park, Taegu (KR); Songcheol Hong, Taejun (KR); Euisik Yoon, Taejun (KR)

(73) Assignee: Korea Advanced Institute of Science and Technology, Taejun (KR)

( * ) Notice: Subject to any disclaimer, the term of this patent is extended or adjusted under 35 U.S.C. 154(b) by 0 days.

(21) Appl. No.: 10/777,941

(22) Filed: Feb. 12, 2004

(65) Prior Publication Data

US 2004/0159786 A1   Aug. 19, 2004

Related U.S. Application Data

(62) Division of application No. 09/598,656, filed on Jun. 21, 2000, now abandoned.

(30) Foreign Application Priority Data

Jun. 21, 1999   (KR) ................................. 1999-23367

(51) Int. Cl.
  *G01N 23/00* (2006.01)
  *G21K 7/00* (2006.01)
(52) U.S. Cl. ...................................................... 250/306
(58) Field of Classification Search .................... 216/2; 148/33.3; 250/306, 307; 324/715, 750, 324/754; 73/105
  See application file for complete search history.

(56) References Cited

U.S. PATENT DOCUMENTS

| 4,581,101 A | * | 4/1986 | Senoue et al. ............. 438/706 |
| 4,943,719 A | | 7/1990 | Akamine et al. |
| 4,968,585 A | | 11/1990 | Albrecht et al. |
| 5,021,364 A | | 6/1991 | Akamine et al. |
| 5,386,720 A | * | 2/1995 | Toda et al. ................... 73/105 |
| 5,475,318 A | | 12/1995 | Marcus et al. |
| 5,489,774 A | | 2/1996 | Akamine et al. |
| 5,856,967 A | | 1/1999 | Mamin et al. |

OTHER PUBLICATIONS

Kasap, S.O, "Principles of Electrical Engineering Materials and Devices", 1997, Irwin Publishing, pp. 48-51.*
Tortonese, M. et al. "Atomic Force Microscopy Using a Piezoresistive Cantilever", C.F. Quate et al., *Solid State Sensors and Actuators*, pp. 448-451, (1991).

* cited by examiner

*Primary Examiner*—David A. Vanore
(74) *Attorney, Agent, or Firm*—Akin Gump Strauss Hauer & Feld, LLP

(57) ABSTRACT

A probe is provided for an SPM (Scanning Probe Microscope), and a method is provided for fabricating the probe in which a double side alignment process is not required to simplify the fabricating. The probe includes a cantilever; a body supporting the cantilever; and a tip formed at an end of the cantilever, wherein the cantilever, the body and the tip are made of silicon, and boron is diffused into the cantilever and a predetermined area of the body. The method includes steps of: forming a first mask layer on an area of a silicon substrate to be formed with the body and the tip; etching the silicon substrate in a predetermined depth using the first mask layer to form the tip; removing the first mask and forming a second mask layer on an area of the silicon substrate except for an area to be formed with the body and the cantilever; forming a boron-diffused layer by diffusing boron into an area to be formed with the cantilever and a predetermined area of the body using the second mask; removing the second mask layer and forming a third mask layer on the boron-diffused layer; and etching the silicon substrate using the third mask layer to form the body and the cantilever.

10 Claims, 7 Drawing Sheets

METHOD OF FABRICATING PROBE FOR SCANNING PROBE MICROSCOPE

CROSS-REFERENCE TO RELATED APPLICATION

This is a division of application Ser. No. 09/598,656, filed Jun. 21, 2000, now abandoned.

BACKGROUND OF THE INVENTION

The present invention is directed to a probe used for a scanning probe microscope (hereinafter, referred to as SPM) and a method of fabricating the probe. More particularly, the present invention is directed to a probe for an SPM and a method of fabricating the probe in which a double side alignment process is not required to simplify the fabricating.

The SPM is a microscope capable of observing various shapes on a surface of an object by nano meters that cannot be observed by an optical or electron microscope, and is used widely, now. In recent years, methods for realizing a highly integrated storage device using the SPM have been studied and much used in a photolithography for forming fine patterns. In the SPM, a probe is used to scan a surface of an object.

A general structure of a probe is shown in FIG. 1. FIG. 1 is a photograph of a probe taken by a scanning electron microscope (SEM). The probe includes a cantilever 101, a body 102 supporting the cantilever 101 and a tip 103 formed at the end of the cantilever 101. The cantilever 101 includes two legs of which one ends are connected to a side of the body 102 and of which the other ends are connected to each other, so that the two legs form a triangle. A position where the other ends of the two legs are connected to each other is formed with the tip 103.

The conventional probe is made of silicon dioxide, silicon nitride, metal, silicon and the like. Specifically, silicon is widely used as probe material because of its excellent mechanical characteristic. When the silicon is used as probe material, silicon on insulator (SOI) wafer is usually as a silicon substrate.

An example of fabricating a probe of a AFM (Atomic Force Microscope) using the SOI wafer is described in a paper published with IEEE in 1991 by C. F. Quate et al., entitled "Atomic Force Microscope Using a Piezoresistive Cantilever". According to this paper, a silicon cantilever is fabricated through a double side alignment process, using a silicon dioxide at the center of the SOI wafer as an etching-stopper layer. In this case, the cantilever is made of silicon with an excellent mechanical characteristic to obtain a sharp tip. However, because a complicate double side alignment process is used and a position of the silicon dioxide where etching is stopped is varied according to a thickness of the SOI wafer, a length of the cantilever is not constant. Also, because the SOI wafer is expensive, cost in mass production thereof increases.

An example of fabricating a probe of a AFM (Atomic Force Microscope) using silicon dioxide, silicon nitride, metal and the like except for the silicon is described in U.S. Pat. No. 4,968,585, patented to T. R. Albrecht et. al, on Nov. 6th in 1990 and U.S. Pat. No. 5,021,364, patented to C. F. Quate et. al, on Jun. 4th in 1991. In these patents in which the probe of a AFM is made of silicon dioxide, silicon nitride, metal and the like, the mechanical characteristic of the cantilever is not as good as that of the silicon cantilever and a range in which a thickness of the cantilever can be adjusted is limited. In addition, deposition characteristic of deposited films make the tip not as sharp as the silicon tip.

Therefore, a probe for an SPM and a method of fabricating the probe in which a probe with an excellent performance can be fabricated in simpler processes and in lower cost have been required.

BRIEF SUMMARY OF THE INVENTION

The present invention is made in order to solve the aforementioned problems.

Therefore, An object of the present invention is to provide a method of fabricating a probe in which the probe can be fabricated with more ease and more simplification.

Another object of the present invention is to provide a method of fabricating a probe in lower cost.

Still another object of the present invention is to provide a probe with a more excellent performance.

The above objects can be accomplished by a probe including a cantilever; a body supporting the cantilever; and a tip formed at an end of the cantilever, wherein the cantilever, the body and the tip are made of silicon, and boron is diffused into the cantilever and a predetermined area of the body.

It is preferable that the silicon has a <110> directional crystal structure.

It is more preferable that the boron is diffused into the tip.

Also, the above objects can be accomplished by a method of fabricating a probe including a cantilever, a body supporting the cantilever and a tip formed at an end of the cantilever, the method comprising steps of: forming a first mask layer on an area of a silicon substrate to be formed with the body and the tip; etching the silicon substrate in a predetermined depth using the first mask layer to form the tip; removing the first mask and forming a second mask layer on an area of the silicon substrate except for an area to be formed with the body and the cantilever; forming a boron-diffused layer by diffusing boron into an area to be formed with the cantilever and a predetermined area of the body using the second mask; removing the second mask layer and forming a third mask layer on the boron-diffused layer; and etching the silicon substrate using the third mask layer to form the body and the cantilever.

It is preferable that the silicon substrate has a <110> directional crystal structure.

Also, it is preferable that the first, second and third mask layers are a silicon dioxide.

According to the present invention, it is preferable that the step of etching the silicon substrate to form the tip is performed by an RIE (Reactive Ion Etching) process using SF6, He and O2 gases. A sharpness of the tip can be adjusted by varying a process condition of a constitution ratio of the gases, a power, a pressure and the like during the RIE process.

It is still preferable that the step of forming the boron-diffused layer comprises steps of ion-implanting the boron and diffusing the boron by a heat treatment or a step of diffusing the boron by a heat treatment using a solid source containing the boron. Here, a thickness of the boron-diffused layer is determined by a temperature during the heat treatment and a time of diffusing the boron.

Also, it is preferable that the step of etching the silicon substrate to form the body and the cantilever is performed by an anisotropic etching of the silicon substrate. Here, the boron-diffused layer can serve as an etching-stopper layer.

It is preferable that the anisotropic etching of the silicon substrate is performed by using an etchant selected from the group consisting of EDP (Ethylene Diamine Pyrocathecol), TMAH and KOH.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

FIGS. 2a through 2f are cross-sectional views showing the results of various process steps for forming a silicon probe tip according to the present invention.

Figure 1:
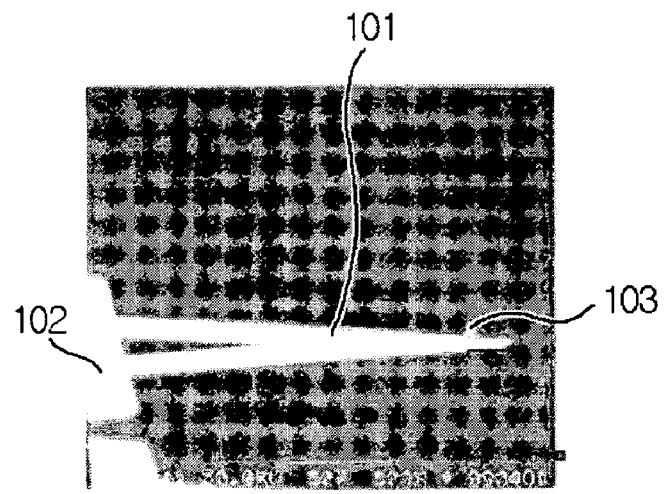
FIG. 1 shows a structure of a general probe.
Figure 2A:
FIGS. 2a through 2f are cross-sectional views showing the results of various process steps for forming silicon probe tip according to the present invention.

First, as shown in FIG. 2a, a silicon substrate 201 is prepared. It is preferable that the silicon substrate has <110> directional crystal structure.

Figure 2B:
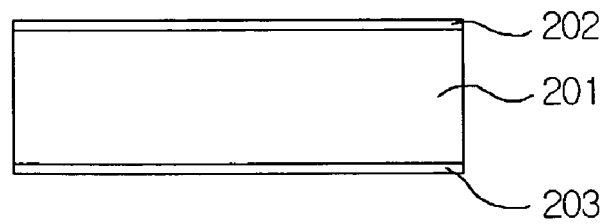

Next, as shown in FIG. 2b, a first mask layer to be used as a mask during etching process for forming a silicon tip is formed on the silicon substrate. It is preferable that the first mask layer is silicon dioxide 202 and 203. The thickness of the silicon dioxide is determined by etching selectivity of the silicon substrate and the silicon dioxide. In the present embodiment, the silicon dioxide is formed 7000 Å thick.

Figure 2C:
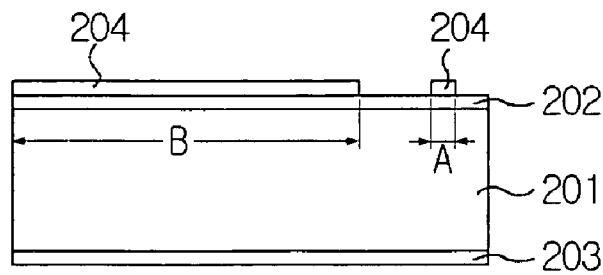

Subsequently, as shown in FIG. 2c, in order to selectively etch the silicon dioxide, photoresist 204 is coated and patterned so that the photoresist remains on a portion A of the silicon dioxide to be formed with a silicon tip and a portion B of the silicon dioxide to be formed with a body supporting the cantilever.

Figure 2D:
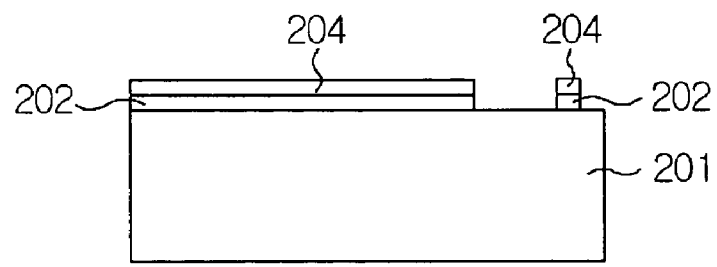

Next, as shown in FIG. 2d, the exposed silicon dioxide is selectively etched using the remained photoresist as a mask. The selective etching is a wet etching using BOE (Buffered Oxide Etchant) as an etchant. At this time, the silicon dioxide 203 under the silicon substrate 201 is etched and removed.

Figure 2E:
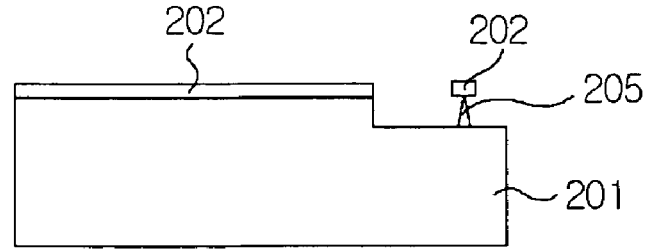

Subsequently, as shown in FIG. 2e, the remained photoresist is removed and the silicon substrate 201 is etched in a predetermined depth using the remained silicon dioxide as a mask to form a silicon tip 205. It is preferable that the etching is performed by RIE (Reactive Ion Etching) method using $SF_6$, He and $O_2$ gases. The etching is performed under such process condition as about 100 W of power and 150 mTorr of pressure. In the etching process, anisotropic etching and isotropic etching are performed at the same time. A sharpness of the silicon tip can be adjusted because if constituent ratio of the gases, the power and the pressure is varied, anisotropic and isotropic etching quantity will be adjusted.

Figure 2F:
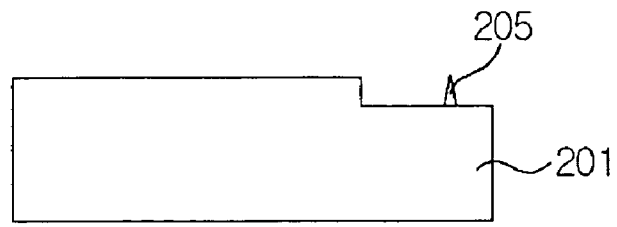

As shown in FIG. 2f, the remained silicon dioxide is removed. The silicon dioxide on the silicon tip can be previously removed by adjusting an etching time during the etching process in FIG. 2e.

FIGS. 3a through 3e are cross-sectional views showing the results of various process steps for forming a boron-diffused layer in the probe according to the present invention.

Figure 3A:
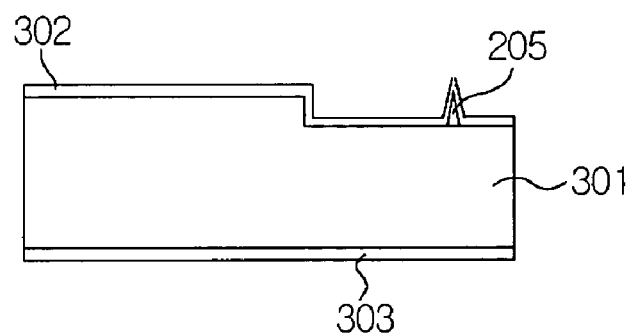
FIGS. 3a through 3e are cross-sectional views showing the results of various process steps for forming a boron-diffused layer in the probe according to the present invention.

First, with reference to FIG. 3a, the silicon substrate with the silicon tip 205 formed as in FIG. 2f is formed thereon with a second mask layer to be used as a mask in selectively forming a boron-diffused layer. It is preferable that the second mask layer is silicon dioxide 302 and 303. In the present embodiment, it is preferable that a thickness of the silicon dioxide is 1 μm. In this case, the silicon dioxide is not formed on the end of the silicon tip as well as on the side of the silicon tip due to stress, and this enables the end of the silicon tip to become sharper. When formed at temperature not higher than about 950° C., the end of the silicon tip becomes sharpest. Also, the silicon dioxide makes the rough side of the silicon tip smooth. Here, reference number 301 indicates a silicon substrate having <110> directional crystal structure described above.

Figure 3B:
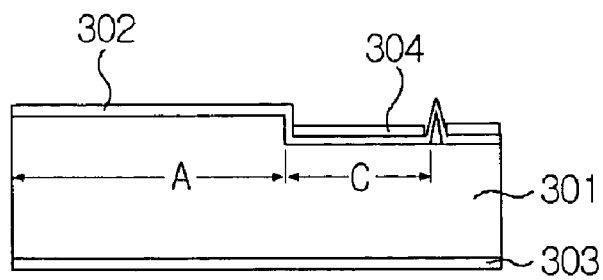

Next, as shown in FIG. 3b, photoresist 304 is coated on the whole resultant surface and the photoresist on portions C to be formed with the probe body and the cantilever.

Figure 3C:
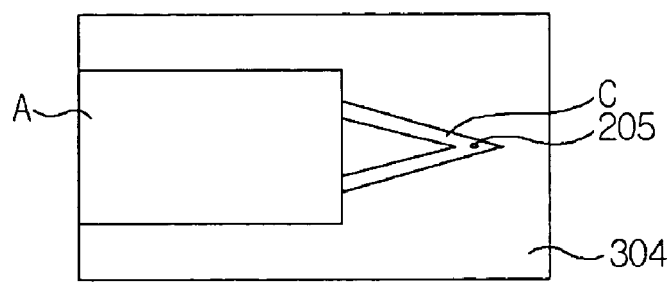

On the other hand, FIG. 3c is a plan view of FIG. 3b, in which the silicon dioxide remains only on portions C to be formed with the probe body and the cantilever. On portions except for the remained silicon dioxide, photoresist 304 is formed. Successively, the silicon dioxide 302 is removed using the remained photoresist as a mask to expose the silicon substrate, and then boron is diffused. At this time, the silicon dioxide on the lower surface of the silicon substrate is removed.

Figure 3D:
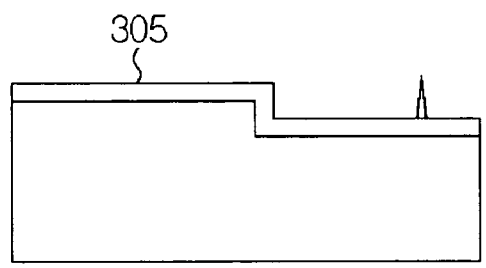

In the present embodiment, the boron can be diffused by ion-implantation of boron and heat treatment, or by heat treatment using a solid source containing boron. The heat treatment for diffusing boron is performed at temperature of about 850° C. through about 1200° C., most preferably at temperature of 1100° C., for 7 hours. A boron-diffused layer 305 as a result is shown in FIG. 3d. A thickness of the boron-diffused layer 305 can be easily adjusted by process temperature and diffusing time. As in the present embodiment, when the diffusion is performed at temperature of 1100 centigrade for 7 hours, a boron-diffused layer having a thickness of 4 μm is formed.

Figure 3E:
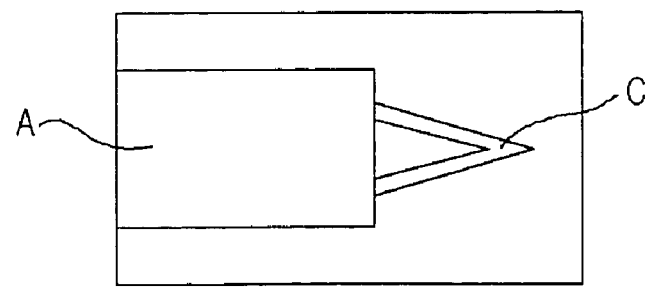

On the other hand, FIG. 3e is a plan view of FIG. 3d, in which boron is diffused only into a portion C to be formed with a cantilever C and a portion A to be formed with a body supporting the cantilever, and the boron-diffused layer 305 serves as a etching-stopper layer in etching the silicon substrate to complete a probe.

FIGS. 4a through 4e are cross-sectional views showing the results of various process steps for forming a cantilever of the probe according to the present invention.

Figure 4A:
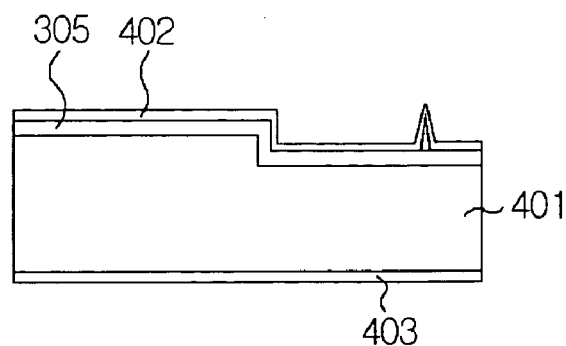
FIGS. 4a through 4e are cross-sectional views showing the results of various process steps for forming a cantilever of the probe according to the present invention.

First, as shown in FIG. 4a, a third mask layer to be used as a mask in anisotropic etching to be performed later is formed on the silicon substrate formed with the boron-diffused layer 305 in FIG. 3e. It is preferable that the third mask layer is silicon dioxide 402 and 403. The silicon dioxide serves as protecting portions not etched in the anisotropic etching. In the present embodiment, it is preferable that a thickness of the silicon dioxide is 1 μm. As in forming the silicon dioxide 302 and 303 to selectively form the boron-diffused layer, the tip becomes sharper in forming the silicon dioxide used as an etching-mask to form the cantilever.

Figure 4B:
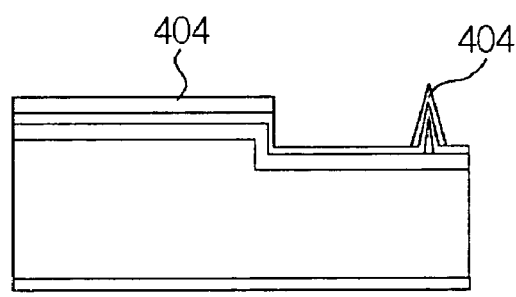

As shown in FIG. 4b, photoresist 404 is coated on the whole resultant surface, and then the photoresist is patterned to cover only portion C to be formed with the cantilever and portion A to be formed with the body supporting the cantilever.

Figure 4C:
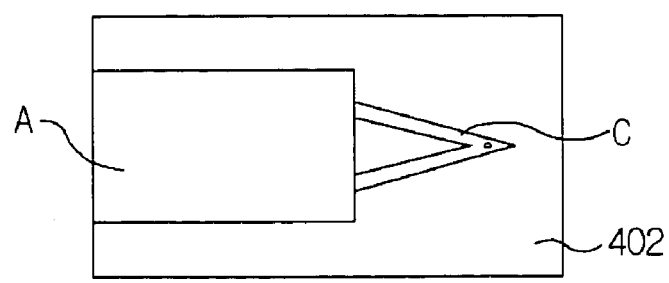

On the other hand, FIG. 4c is a plan view of FIG. 4b, in which the photoresist remains only on portion C to be formed with the cantilever and portion A to be formed with the body supporting the cantilever and the silicon dioxide 402 to be etched is exposed. Successively, the exposed silicon dioxide 402 is etched using the remained photoresist 404. At that time, the silicon dioxide 403 on the lower surface of the silicon substrate is removed at the same time. Successively, the remained photoresist is removed to leave the silicon dioxide only on portion C to be formed with the cantilever and portion A to be formed with the body supporting the cantilever and to expose the rest portion.

Figure 4D:
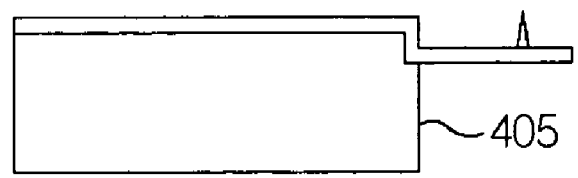

With reference to FIG. 4d, using the silicon dioxide remaining on portion C to be formed with the cantilever and portion A to be formed with the body supporting the cantilever as a mask, the exposed silicon substrate is etched. An EDP (Ethylene Diamine Pyrocathecol) solution which is an anisotropic etchant is used as an etchant, in which the EDP has etching ratio varied with crystal direction of silicon. In the other words, the etching ratio of <111> surface is much lower than that of <100> and <110> surfaces, so that etching is stopped on <111> surface 405. Namely, the silicon substrate is etched in a vertical direction from the surface. This is because unlike silicon having <100> crystal direction, silicon remains on the back surface of the cantilever. Therefore, the probe of a SPM can be fabricated without a double side alignment process. As other etchant, TMAH or KOH can be used for anisotropic etching of the silicon substrate.

Figure 4E:
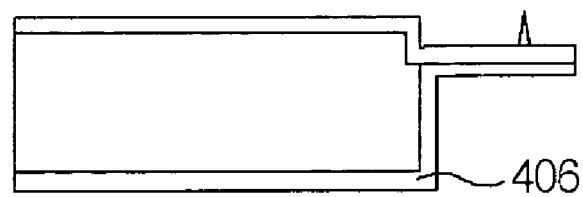

In another embodiment, as shown in FIG. 4e, gold(Au) 406 may be additionally formed on the back surface of the cantilever. This is for intensifying a reflecting effect of light, in which movement of the cantilever is detected by irradiating light to the back surface of the cantilever and measuring the phase of the reflected light. Also, before Au is deposited, Titanium(Ti)(not shown) may be deposited so as to increase the adhesion power between the silicon substrate and the boron-diffused layer.

Figure 5A:
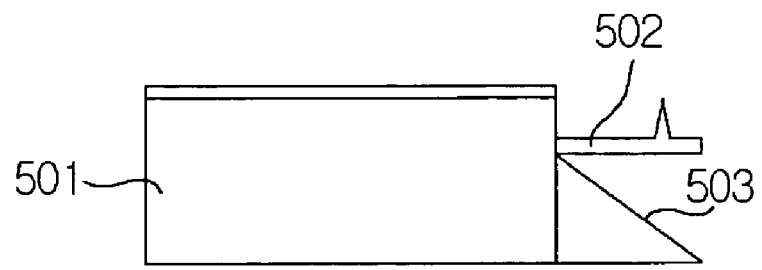
FIGS. 5a through 5c are cross-sectional views showing the shapes of probes formed by anisotropic etching with respect to the directions of silicon crystal structures.
Figure 5B:
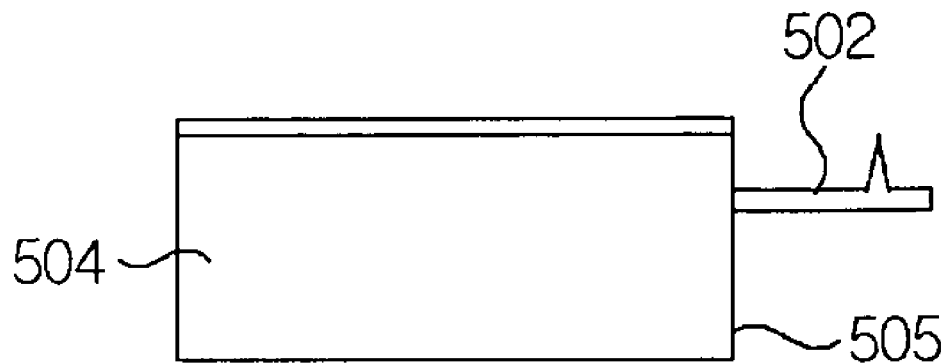
Figure 5C:
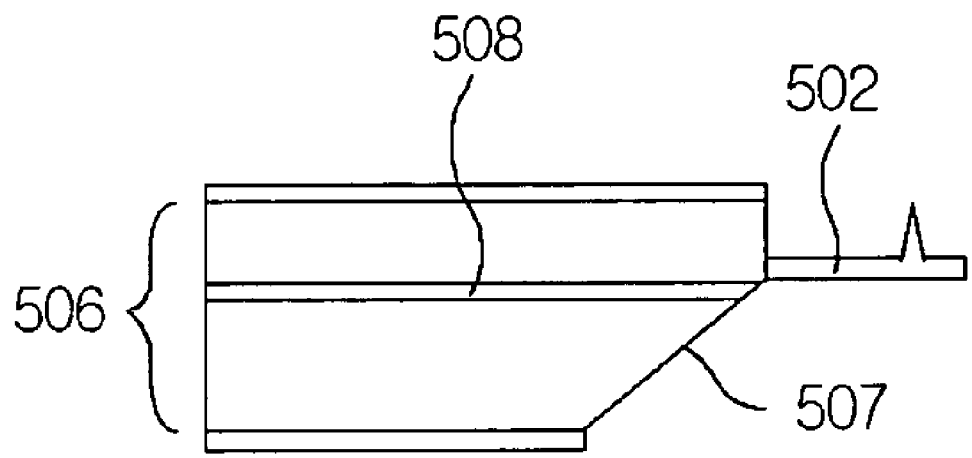

On the other hand, FIGS. 5a through 5c are cross-sectional views showing the shapes of probes formed by anisotropic etching with respect to the directions of silicon crystal structures, in which the present invention using a silicon substrate with <110> directional crystal structure and the conventional art are compared.

First, in FIG. 5a illustrating the case in which the silicon substrate 501 having a <100> directional crystal structure is used, when the silicon substrate is anisotropically etched, a <111> surface of an etching-stopper surface on the back surface of the silicon cantilever 502 makes silicon remain. In this case, there is a problem that such cantilever cannot be used in the conventional SPM in which movement of the cantilever is detected by irradiating light to the back surface of the cantilever and measuring the phase of the reflected light. For solving the problem, it is required to pattern and anisotropically etch the back side of the wafer. However, such process makes the method complicated, and in addition, a position of the tip of the cantilever is varied with a thickness of the wafer to deteriorate characteristics of the cantilever.

Next, FIG. 5b illustrates the case that the silicon substrate 504 having a <110> directional crystal structure is used, in which <111> surface of etching-stopper surface 505 is formed in a vertical direction from the end of the cantilever 502 by anisotropically etching the silicon substrate. Therefore, the problem that silicon remains on the back surface of the cantilever can be solved, and in addition, etching is stopped at the end of the cantilever.

Also, FIG. 5c illustrates the case that the SOI wafer 506 is used as a substrate. In FIG. 5c, when the double side alignment process aligning the front and back surfaces of the wafer is used, the <111> surface of an etching-stopper surface is not formed on the back surface of the cantilever and the silicon dioxide layer 508 between silicon bulks serves as an etching-stopper layer. In this case, as in the present invention, silicon does not remain on the back surface of the cantilever. However, the double side alignment process is necessary to complicate the processes, and a length of the cantilever is varied with variation of a thickness of the wafer. Therefore, when using the silicon substrate with <110> directional crystal structure as in the present invention, a probe with an excellent performance can be easily fabricated without the complicated double side alignment process.

On the other hand, the SPM of the present invention comprises an AFM (Atomic Force Microscope), an STM (Scanning Tunneling Microscope), an MFM (Magnetic Force Microscope), an EFM (Electrostatic Force Microscope), an SCM (Scanning Capacitance Microscope), an SNOM (Scanning Near-field Optical Microscope), and the like. The probe according to the present invention may be used for the aforementioned microscopes.

As described above, advantages of a probe and a method of fabricating the probe according to the present invention are as follows.

First, because silicon wafer having a <110> directional crystal structure is used as a probe material, the double side alignment process required in using the conventional SOI wafer is not necessary so as to simplify the processes.

Second, in forming the silicon dioxide used as a mask after forming the tip, the silicon dioxide has functions sharpening the tip and smoothing the rough surface of the tip in addition to the function as a mask. The advantage of sharpening the tip is accomplished on the basis of a fact that a speed for forming the silicon dioxide is higher at the end of the tip than at the side surface of the tip.

Third, because the cantilever is formed using the boron-diffused layer, the thickness of the cantilever can be adjusted with the diffusing temperature and time. Because the boron can be used as an etching-stopper layer, a silicon cantilever can be fabricated without the conventional SOI wafer used. Also, the fabrication cost can be decreased because the expensive SOI wafer is not used.

Namely, according to the present invention described above in detail, the probe can be fabricated with more ease and more simplification, and in lower cost. In addition, a probe with a more excellent performance can be obtained.

Although representative embodiments of a probe of a SPM and a method of fabricating the probe according to the present invention have been disclosed for illustrative purposes with reference to the appended drawings, the present invention should not be limited to the embodiments. Those who are skilled in the art will appreciate that various modifications, additions and substitutions are possible without departing from the scope and spirit of the present invention as defined in the accompanying claims and the equivalents thereof.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of fabricating a probe including a cantilever, a body supporting said cantilever and a tip formed at an end of the cantilever, comprising the steps of:
    (a) providing a silicon substrate having <110> directional crystal structure as a starting wafer, wherein the substrate has an upper surface and a lower surface;
    (b) forming a first mask layer on the upper and lower surfaces of the silicon substrate;
    (c) coating a first photoresist on the first mask layer on the upper surface of the silicon substrate and patterning th photoresist to leave portions of the first photoresist defining the tip and the body;
    (d) etching the silicon substrate using the remaining first photoresist as a mask to remove portions of the first mask layer;
    (e) removing the remaining first photoresist;
    (f) etching the silicon substrate in a predetermined depth using the first mask layer remaining on the upper surface of the silicon substrate as a mask to form the tip;
    (g) removing the remaining first mask layer;
    (h) forming a second mask layer on an area of the silicon substrate except for an area to be formed with the body and the cantilever;
    (i) forming a boron-diffused layer by diffusing boron into the silicon substrate using the second mask layer as a mask so that the boron is diffused only into a portion of he silicon substrate to be formed with the cantilever and the body;
    (j) removing the second mask layer;
    (k) forming a third mask layer on the upper and lower surfaces of the silicon substrate;
    (l) coating a second photoresist on the third layer on the upper surface of the silicon substrate and patterning the photoresist to cover only portions of the second photoresist to be formed with the cantilever and the body;
    (m) etching the silicon substrate using the remaining second photoresist as a mask to remove portions of the third mask layer;
    (n) removing the remaining second photoresist and third mask layer on the lower surface of the substrate; and
    (o) performing an anisotropic etching of the silicon substrate using the third mask layer remaining on the upper surface of the silicon substrate as a mask so that the silicon substrate is etched in a vertical direction from the upper and lower surfaces of the substrate thereby forming the body and the cantilever.

2. The method of fabricating a probe according to claim 1, wherein the first, second and third mask layers are a silicon dioxide.

3. The method of fabricating a probe according to claim 1, wherein step (f) of etching the silicon substrate to form the tip is performed by a reactive ion etching process using $SbF_6$, He and $O_2$ gases.

4. The method of fabricating a probe according to claim 1, wherein step (i) of forming the boron-diffused layer comprises steps of ion-implanting the boron and diffusing the boron by a heat treatment.

5. The method of fabricating a probe according to claim 1, wherein step (i) of forming the boron-diffused layer comprises a step of diffusing the boron by a heat treatment using a solid source containing the boron.

6. The method of fabricating a probe according to claim 1, wherein the boron-diffused layer serves as an etching-stopper layer during the anisotropic etching.

7. The method of fabricating a probe according to claim 1, wherein the anisotropic etching of the silicon substrate is performed by using an etchant selected from the group consisting of ethylene diamine pyrocathecol, tetramethyl ammonium hydroxide and potassium hydroxide.

8. The method of fabricating a probe according to claim 3, wherein a sharpness of the tip is adjusted by varying a process condition of a constitution ratio of the gases, a power, or a pressure during the reactive ion etching process.

9. The method of fabricating a probe according to claim 4, wherein a thickness of the boron-diffused layer is determined by a temperature during the heat treatment and a time of diffusing the boron.

10. The method of fabricating a probe according to claim 5, wherein a thickness of the boron-diffused layer is determined by a temperature during the heat treatment and a time of diffusing the boron.

* * * * *